United States Patent [19]
Bart et al.

[11] Patent Number: 5,142,920
[45] Date of Patent: Sep. 1, 1992

[54] DISSOLUTION CELL AND APPARATUS FOR DETERMINING SOLIDS-DISSOLVING KINETICS

[75] Inventors: Gilles Bart, Donnery; Roland Dequin; Jacques Paturat, both of Briare, all of France

[73] Assignee: Prolabo, Paris, France

[21] Appl. No.: 631,282

[22] Filed: Dec. 20, 1990

[30] Foreign Application Priority Data

Dec. 20, 1989 [FR] France .................. 89 17214

[51] Int. Cl.$^5$ .................................. G01D 21/00
[52] U.S. Cl. ........................... 73/866; 210/451
[58] Field of Search ............ 73/866; 210/85, 251, 210/497.01, 451, 453

[56] References Cited

U.S. PATENT DOCUMENTS

| | | | |
|---|---|---|---|
| 2,118,295 | 5/1938 | Crawford et al. | 210/251 X |
| 2,598,818 | 6/1952 | Muirhead | 210/453 X |
| 3,620,675 | 11/1971 | Olson | 23/230 R |
| 3,802,272 | 4/1974 | Bischoff | 73/866 |
| 4,247,298 | 1/1981 | Rippie | 23/230 R |
| 4,856,909 | 8/1989 | Mehta et al. | 366/208 |

FOREIGN PATENT DOCUMENTS

0043226 1/1982 European Pat. Off. .

Primary Examiner—Jerry W. Myracle
Attorney, Agent, or Firm—Burns, Doane, Swecker & Mathis

[57] ABSTRACT

A dissolution cell for determining the kinetics of dissolution of a solid substance in a particular liquid, includes (a) a housing receptacle having a closed bottom end and an open top end, an interior of such receptacle defining (i) a lowermost upwardly diverging conical zone provided with liquid inlet means extending from a tip of the conical zone through the bottom end of the receptacle, (ii) a first essentially cylindrical zone surmounting the conical zone and (iii) a second essentially cylindrical zone surmounting the first essentially cylindrical zone, having a cross-sectional diameter greater than that of the first essentially cylindrical zone and being in communicating relationship therewith, such conical zone (i) and such first essentially cylindrical zone (ii) defining a chamber for the dissolution of a solid substance in a liquid solvent, (b) a closure leak-proofedly secured to the open end of the receptacle and provided with a solute outlet means, and (c) filtration means secured between such closure and an area of communicating relationship between the first and the second essentially cylindrical zones, so as to be disposed in a pathway for the solute extending from the dissolution chamber to the solute outlet means.

14 Claims, 2 Drawing Sheets

DISSOLUTION CELL AND APPARATUS FOR DETERMINING SOLIDS-DISSOLVING KINETICS

BACKGROUND OF THE INVENTION

1. Field of the Invention

The present invention relates to a novel dissolution cell for solids.

This invention also relates to an apparatus for studying the kinetics of dissolution of a solid, which apparatus comprises at least one such cell.

2. Description of the Prior Art

In research and in industry, it is often necessary to determine the speed at which a soluble solid substance is dissolved by a solvent. Such a requirement is experienced, particularly, in research in pharmacology and biology. For example, in pharmacology the measurement of the speed, or rate, at which a solid substance dissolves in a solvent is necessary for determining the efficacy and the characteristics of this solid substance. Thus, the speed at which a tablet dissolves in the digestive tract influences the speed at which the active components of the tablet will enter the bloodstream of the patient (bioavailability). It is therefore necessary to measure this speed precisely in order to define both the composition and the presentation of a medicament in solid form, such that the dosage form gives the expected effect.

In industry, the measurement of the speed of dissolution of a tablet is frequently used in manufacturing control procedures.

A pharmaceutical tablet typically, comprises two principal components, namely, the active principle and a binder therefor which permits shaping the tablet and imparting mechanical strength thereto. The binder also confines the active principle and releases its gradually after absorption.

The methods for studying the kinetics o dissolution of a tablet, more generally of a solid, are defined by the European Pharmacopoeia Commission in the pharmacopoeia note for 1990, paragraph V.5.4.A. entitled "Continuous flow cell method".

In particular, the pharmacopoeia note specifies the requirements for studying the kinetics of dissolution of a solid substance by the continuous flow cell method.

The apparatus described is principally a cell, made of glass or a plastic material, whose useful volume is a cylinder, and at the lower end of the cylinder a cone is attached. The cone is pierced by a hole at its tip for the supply of the solvent. A circular filter, for example made of glass microfibers, is secured to the upper end of the cylinder over the entire cross-section of the useful volume. In order to distribute the solvent uniformly over the entire cross-section of the cell, the conical section is filled with a packing, for example of spherical glass balls. After passing through the filter, the solute is removed at the top end of the cell and then directed to a sample-collecting system or directly to an analyzer.

The pharmacopoeia note specifies the dimensional characteristics of the useful volume of the cell and of the cone and recommends flushing the cell with a continuous flowstream of solvent at a flowrate measured with a precision of 5%.

In order to obtain good analytical results, it is necessary to retain all the particles of binder present in the cell, and for this purpose filters are used, the porosity of which is on the order of a few microns. Thus, this results in the phenomenon of clogging of the filter, which gives rise to an increase in the head losses of the solvent/solute circuit and consequently produces an increase in the pressure inside the cell.

In order to limit this phenomenon, it is therefore important to provide a large filtration surface. It is also sometimes necessary, in specific cases, to be able to increase the filtration surface for a given cell.

Nonetheless, this is impossible using a cell such as that described in the pharmacopoeia note, since the surface of the filter is determined by the internal cross-section of the cell.

Moreover, it is often necessary to determine with precision the parameters such as temperature, pressure, pH of the liquid medium present in the cell, it being possible for variations in these parameters to have a very strong influence on the kinetics of dissolution of the solid substance.

Also, a cell such as described above does not permit simple introduction of one or more measurement probes into the liquid medium in the cell.

SUMMARY OF THE INVENTION

Accordingly, a major object of the present invention is the provision of a novel dissolution cell and an apparatus for determining the kinetics of dissolution of a solid and comprising at least one such novel cell, which conspicuously ameliorate the above disadvantages and drawbacks to date characterizing the state of this art.

Another object of the present invention is the provision of a novel dissolution cell for solids which provides a greater filtration surface and which additionally permits varying the filtration surface of the cell depending on the solid under examination.

Yet another object of this invention is the provision of a novel dissolution cell which permits, depending on other parameters thereof, introducing at least one measurement probe into the liquid medium in the cell.

Still another object of this invention is the provision of apparatus for measuring the kinetics of dissolution of a solid, in which the solvent flowrate is perfectly regular.

Briefly, the present invention features a dissolution cell for solids which comprises:

(a) a housing receptacle closed at the bottom end and open at the top end and internally confining, from bottom to top:

(i) a diverging conical chamber having inlet means for liquid at its tip, said chamber containing a packing for distributing the liquid and being surmounted by a first cylindrical zone, (ii) said conical chamber and said first cylindrical zone defining the dissolution chamber, (iii) a second essentially cylindrical zone surmounting said first cylindrical zone, the first zone having a cross-section smaller than that of the second zone, the said zones being connected by means of a shoulder;

(b) a closure adapted to fit in a leakproof manner into the open end of the housing receptacle and comprising outlet means for the solute; and (c) filtration means secured between the closure and the shoulder, such filtration means being disposed along the pathway of the solute between the dissolution chamber and the outlet means for the solute.

DETAILED DESCRIPTION OF THE PREFERRED EMBODIMENTS OF THE INVENTION

Figure 1:
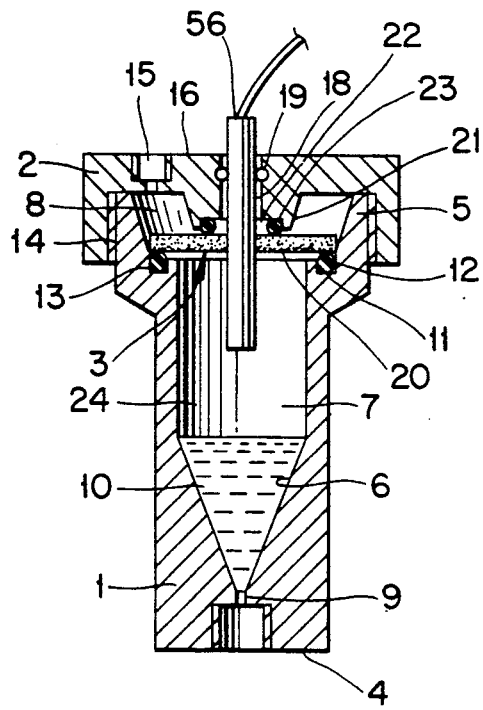
FIG. 1 is a longitudinal sectional view of one embodiment of a dissolution cell according to the present invention.

More particularly according to the present invention, in one preferred embodiment thereof, the filtration means comprises a tubular filter, for example i the form of a hollow cylinder.

Such tubular filter can be fabricated from various materials commonly used, such as porous ceramic material, porous ceramic material impregnated with steel, stainless steel wires, etc. The tubular filter preferably comprises glass microfibers which are mutually arranged by any known means such as to constitute a textile article, for example of the fabric, cloth, nonwoven, knit type.

The closure of the cell of the present invention advantageously comprises passageway means for introducing at least one measurement probe into the dissolution chamber. The measurement probe, per se known to this art, enables monitoring of the development or controlling various parameters of the liquid medium present in the cell, such as temperature, pH, pressure.

In one preferred embodiment of the cell according to the invention, the closure can be secured onto the open end of the housing receptacle, about the outside periphery thereof. In this case, it can be force-fit; preferably the closure is screwed onto the open end of the housing receptacle, which in this case is externally threaded for such purpose.

In another preferred embodiment of the invention, the closure is secured to the open end of the housing receptacle, but internally therein.

In this embodiment, the closure is inserted by force into the open end of the housing receptacle and advantageously comprises, from the outside to the inside of the cell, a body of a cross-section essentially equal to that of the second cylindrical tube in the housing receptacle and a head of a cross-section smaller than that of the body. The outlet means for the solute comprise a tubular passageway extending completely through the body and opening into the interspace located between the head and the wall member of the housing receptacle.

The closure preferably comprises, between the body and the head, a collection zone defined by, for example, an annular groove.

The closure can be constructed of various materials which exhibit good chemical inertness such as not to disrupt the measurements being carried out. Exemplary such materials include polytetrafluoroethylene, organosilicic polymers, and the like.

The housing receptacle can be constructed of various materials which also exhibit, for the same reasons good chemical inertness and which are preferably transparent, such as glass, plastic materials such as polyvinyl chloride, polymethyl methacrylate, etc.

In order to ensure that the binder particles present in the dissolution chamber cannot escape therefrom to be directed towards the analysis apparatus, it is necessary that there exists a certain leakproofness between the housing receptacle and the filter and/or between the closure and the filter.

Such leakproofness can be provided by means of annular ribs borne by the shoulder and the closure, the filter being secured between the closure and the shoulder by these ribs. Due to the flexibility of the material constituting the filter, the ribs penetrate into the latter during assembly of the cell and the leakproofness of the dissolution chamber with respect to the binder particles is assured.

The leakproofness is preferably provided by means of seals, in most cases O-ring seals.

The solid substance whose speed of dissolution it is desired to determine can be place in the dissolution chamber directly, on or in the bed of spherical glass balls. It can thus be retained by any suitable means such as, for example, a basket, as described in the pharmacopoeia note.

The present invention also features the kinetics of dissolution of a solid and which comprises at least one dissolution cell as described above, with pumping means being associated with each cell.

Pumping means which permit the solvent to be delivered at a precise and regular flowrate are particularly suitable.

The apparatus of the invention is advantageously such that the pumping means comprise at least two pistons mounted opposite each other and displaced by a cam turning about an axis perpendicular to the axis of displacement of the pistons, and return means associated with each piston.

The dissolution cell for a solid and the apparatus comprising such cell can be used each time it is necessary to determine the kinetics of dissolution of a solid in a solvent. They are intended, in particular, for determining the kinetics of dissolution of pharmaceuticals in solid form, such as tablets.

Referring specifically to the Figures of Drawing, given purely for purposes of illustration and not drawn to any particular scale, in FIG. 1 is shown a solids dissolution cell comprising a housing receptacle 1, a closure 2 and filtration means 3. The receptacle 1 is closed at its bottom end 4 and open at the top end 5. Disposed within the housing receptacle 1, from bottom to top, is a conical chamber 6, a first cylindrical zone 7 and a second cylindrical zone 8.

The conical zone 6 of the housing receptacle 1 is divergent from bottom to top, and it is provided with, at the tip of the cone, inlet means for the liquid comprising a conduit 9. At the base of the receptacle 1, the conduit 9 is advantageously tapped, in order to permit the straightforward fitting, by means of a connector, of the conduit for supply of liquid.

The conical zone 6 of the receptacle 1 contains a packing 10 intended to distribute the liquid uniformly over the entire cross-section within the receptacle. This packing 10 is typically composed of spherical glass beads.

In this embodiment, the solid substance to be analyzed can be placed directly onto or within the packing 10 of spherical glass beads.

Above the conical zone 6, the receptacle 1 provides the first cylindrical zone 7, surmounted by the second cylindrical zone 8. The first cylindrical zone 7 has a diameter equal to the diameter of the base of the cone and the second cylindrical zone 8 has a diameter greater than that of the first cylindrical zone 7. Due to the difference in dimensions of their diameters, the first cylindrical zone 7 has a cross-section smaller than the cross-section of the second cylindrical zone 8, the cylindrical zones 7 and 8 communicating and being connected by way of a shoulder 11. The shoulder 11 advantageously has a groove 12 adapted to receive a leakproofing seal 13.

The conical zone 6 and the first cylindrical zone 7 form the dissolution chamber 24 of the dissolution cell.

The closure 2 in the illustrated embodiment shown, is fitted to the open end 5 of the receptacle 1, to the outside of the latter by screwing, the receptacle 1 being provided on its outer surface with a threaded zone 14.

The closure 2 comprises outlet means for the solute, which means include a passageway 15. The passageway 15 is advantageously tapped in the vicinity of the upper surface 16 of the closure 2 in order to permit the simple fitting, by means of a connector, of the conduit for conveying the solute to an analysis apparatus.

The closure 2 also comprises passageway means 18 for introducing into the cell at least one measurement probe 56. A seat 19 is provided for positioning a leakproofing seal, for example an O-ring seal, in order to ensure leakproofness between the closure 2 and the measurement probe 56.

The cell 1 according to the invention is provided with filtration means 3 comprising a filter 20 secured between the closure 2, which is in this case provided with a boss 21, and the shoulder 11 of the receptacle 1. A seat 22 is provided in the boss 21 of the closure 2 in order to position a seal 23 for ensuring leakproofness between the filter 20 and the closure 2.

The filter 20 is thus positioned in the pathway of the solute between the dissolution chamber 24 and the passageway 15 for the outlet of the solute to be transferred into an analysis apparatus.

The filter 20 is tubular and fabricated from glass microfibers which are mutually assembled by means of a binder resin.

The filter 20 can exhibit a porosity close to 1 1.

The filter 20, in the embodiment shown in FIG. 1, has a small height with respect to its external diameter. It is possible to position, in the dissolution cell shown, a filter 20 of a greater height, in which case the closure 2 will be screwed down to a lesser extent on the threaded zone 14 situated on the outer surface of the housing receptacle 1.

Figure 2:
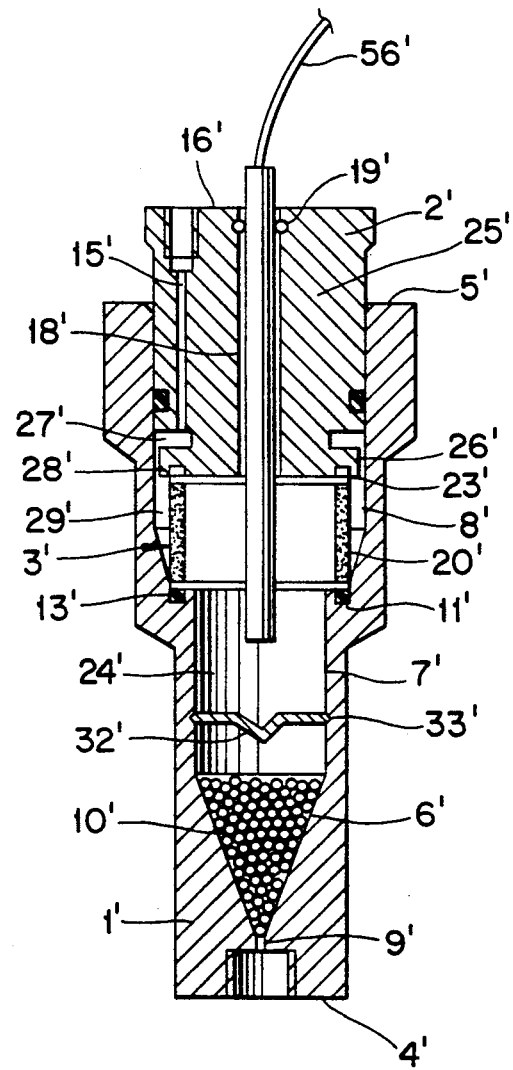
FIG. 2 is a longitudinal sectional view of another embodiment of a dissolution cell according to the present invention.

The dissolution cell shown in FIG. 2 is another preferred embodiment of the invention. The cell comprises a receptacle 1', analogous to that in the embodiment in FIG. 1', comprising a conical zone 6', a first 7' and second 8' cylindrical zone. A conduit 9' for introduction of liquid opens out at the tip of the conical zone 6' which contains a packing 10' of spherical glass beads.

As above described, the first cylindrical zone 7' and the second cylindrical zone 8' are connected by way of a shoulder 11', and the conical zone 6' and the first cylindrical zone 7' define the dissolution chamber 24' of the dissolution cell.

In this embodiment, the closure 2' is fitted to the open end 5' of the receptacle 1' on the inside of the latter, by being inserted into the second cylindrical zone 8.

The closure 2' comprises, from the outside to the inside of the dissolution cell, a body 25' of a cross-section essentially equal to that of the second cylindrical zone 8', a head 26' of a cross-section smaller than that of the body 25' and a collecting zone 27' formed by a groove situated between the body 25' and the head 26' of the closure 2'.

The outlet means for the solute comprise a conduit 15 extending through the body 25' of the closure 2' and opening, by way of the groove 27', into the space 28' situated between the head 26' and the wall of the receptacle 1'. The conduit 15' is of course tapped in the vicinity of the upper face 16' of the closure 2' in order to permit the fitting of a conduit by means of a connector.

The filtration means 3' comprises a tubular filter 20', essentially cylindrical, secured between the head 26' of the closure 2' and the shoulder 11' of the receptacle 1'.

The annular space 29' situated between the filter 20' and the wall of the receptacle 1' is then communicating with the conduit 15' by way of the space 28' and of the collecting zone 27'.

The tubular filter 20' makes it possible to provide a large filtration surface, on the one hand, and, on the other, permits varying the filtration surface for a given cell. Indeed, by placing in the dissolution cell, between the head 26' of the closure 2' and the shoulder 11' of the receptacle 1', filters 20' of different heights, it is possible to vary the filtration surface of the dissolution cell. Of course, depending on the height of the filter 20', the closure 2' will extend into the second cylindrical zone 8' to a greater or lesser extent.

O-ring seals 13', 23' ensure leakproofness, on the one hand, between the filter 20' and the shoulder 11' and, on the other, between the filter 20' and the head 26' of the closure 2'.

The closure 2' comprises, as described above, passageway means 18' for introducing into the dissolution cell at least one measurement probe 56', and a seat 19' for positioning a seal adapted to ensure leakproofness between the closure 2 and the measurement probe 56'.

The dissolution cell of this embodiment is provided with means for holding a solid sample. These means comprise a basket 32', of a type commonly used, secured by notches 33' formed in the wall of the first cylindrical zone 7' of the receptacle 1'.

Figure 3:
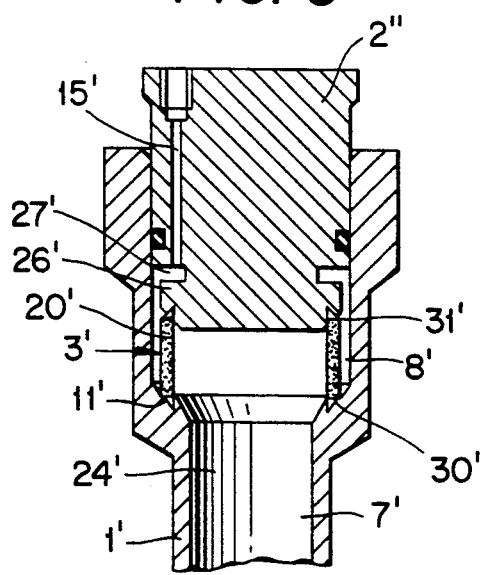
FIG. 3 is a longitudinal, partial sectional view of one embodiment of the leakproofing means, between the filter and the closure as well as between the filter and the housing receptacle, comprising a dissolution cell of this invention.

The embodiment of the dissolution cell shown in FIG. 3 is analogous to that of FIG. 2, but the closure 2' does not have any passageway means for a measurement probe.

In this embodiment, the leakproofing means between the filter 20 and the shoulder 11 of the receptacle 1 and between the filter 20 and the head 26 of the closure 2 are formed by annular ribs 30, 31 respectively borne by the shoulder 11 and the head 26 of the closure 2. During assembly, the ribs 30, 31 penetrate slightly into the filter 20 and thereby ensure leakproofness of the dissolution chamber 24 with respect to the binder particles.

Figure 4:
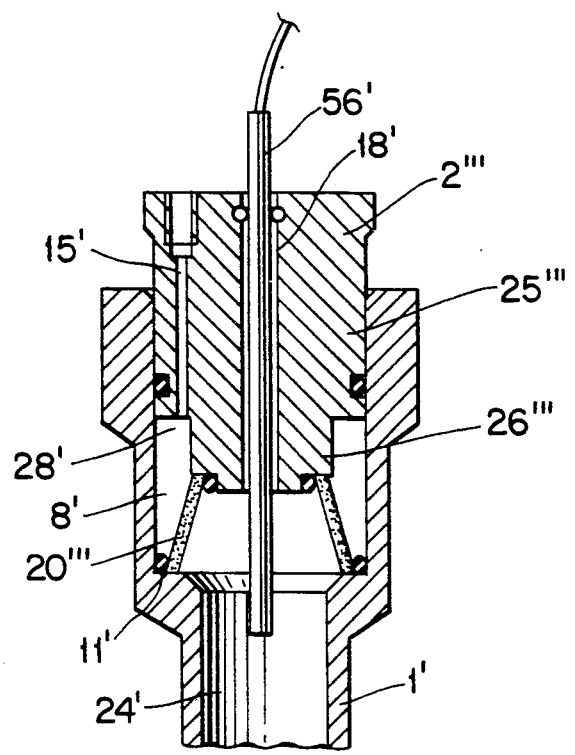
FIG. 4 is a longitudinal, partial sectional view of one embodiment of the filtration means comprising a dissolution cell of this invention.

The dissolution call of the embodiment of FIG. 4 comprises a tubular filter 20' in the form of a truncated cone and the closure 2' does not have any collecting zone between the head 26' and the body 25'. The filter 20' in the form of a truncated once also permits increasing the filtration surface of the dissolution cell.

Figure 5:
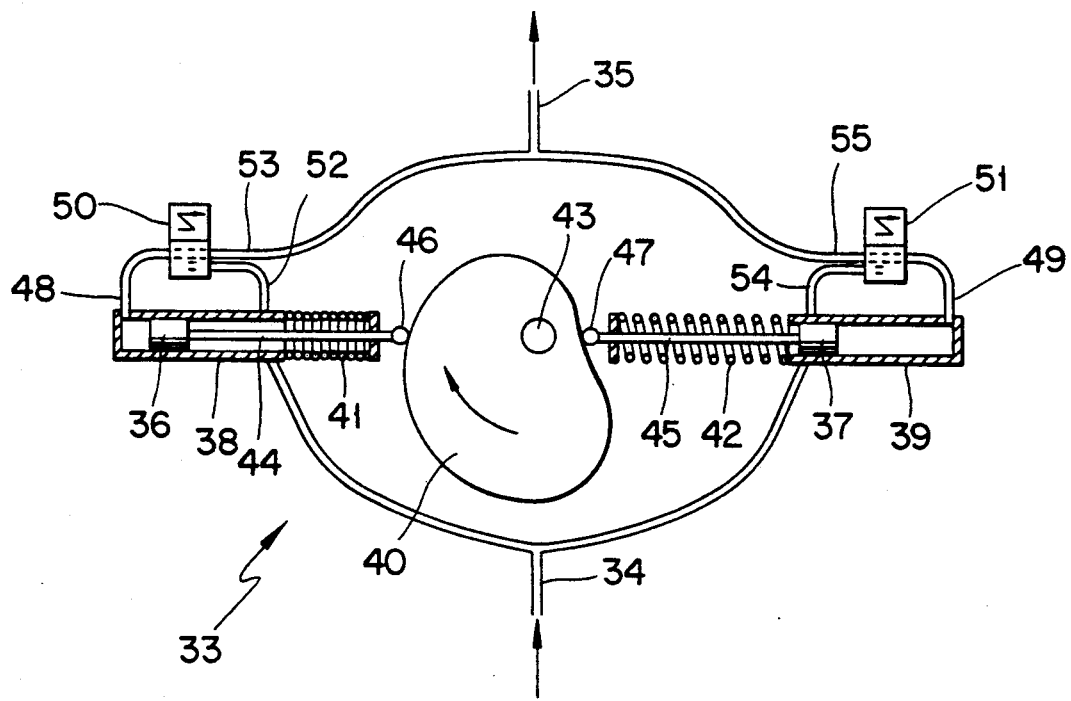
FIG. 5 is a longitudinal sectional view of one embodiment of the pumping means of apparatus according to the present invention for determining the kinetics of dissolution of a solid material.

FIG. 5 shows diagrammatically the pumping means 33 of the apparatus according to the present invention for determining the kinetics of dissolution of a solid.

The pumping means 33 is connected by means of the conduit 34 to a liquid supply reservoir and by means of the conduit 35 to the conduit 9 for introduction of the liquid into the dissolution cell.

The pumping means 33 comprise two pistons 36, 37, mounted opposite each other, and displaced in two cylinders 38, 39. The pistons 36, 37 are moved in an alternating linear movement by means of a face cam 40, provided with a suitable profile, with which there are associated return means including two springs 41, 42. The pistons 36, 37 are mounted in a symmetrical manner relative to the axis 43 of rotation of the cam 40.

Each rod 44, 45 of the pistons 36, 37 is guided linearly and is provided with an anti-rotation device. The rods 44, 45 of the pistons 36, 37 bear on the cam 40 by way of rollers 46, 47. The permanent contact between the rollers 46, 47 and the cam 40 is ensured by the springs 41, 42.

The axis 43 of the cam 40 is driven in rotation, and it is perpendicular to the axis of displacement of the pistons 36, 37. The axis 43 can be driven by means of a motor and a gear, for example by a belt or by pinions. In order to prevent play or sliding, the cam 40 is preferably mounted directly on the output shaft of a geared motor of slow, constant and precisely known speed.

Each cylinder 38, 39 has its outside end 48, 49 connected to a three-way solenoid value 50, 51 with two positions. The outputs 52 and 54 of the solenoid valves 50, 51 are connected to each other and are in communication with the liquid supply reservoir by way of the conduit 34, and the outputs 53 and 55 are connected to each other and are in communication with the dissolution cell by way of the conduit 35.

The maneuvering of the solenoid valves 50, 51 is controlled by means of electric contacts activated at very precise angular positions of the cam 40.

The movement of the two pistons 36, 37 is determined by the shape of the cam 40. The profile of the latter is defined in such manner that the instantaneous sum of the forward speeds of the pistons is constant.

The flowrate obtained with such pumping means is perfectly regular, even in the event of very low flowrates, and is independent of the delivery pressure. Such pumping means are also volumetric, one cam turn delivering two similar cylinder volumes, and if the speed of rotation of the cam is known, it is quite easy to determine with precision the flowrate of liquid intended for delivery to the dissolution cell.

The dissolution cell for solids and the dissolution apparatus comprised thereof present numerous advantages.

Thus, the dissolution cell makes it possible to provide a large filtration surface by virtue of the presence of a tubular filter, this being particularly advantageous for limiting the disadvantages associated with clogging of the filter by the binder particles.

Moreover, by reason of its design, the cell permits simple assembly and disassembly. In addition, the option of introducing measurement probes into the dissolution chamber permits controlling with precision the operating conditions of the dissolution of a solid substance.

The apparatus according to the invention presents the advantage of permitting particularly uniform conditions of flow of the liquid into the cell, the flow of liquid being non-pulsed and being of a volume flowrate known with precision.

The dissolution cell and the dissolution apparatus according to the invention are particularly useful for determining the kinetics of dissolution of solids in the pharmaceutical industry.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A dissolution cell for determining the kinetics of dissolution of a solid substance in a particular liquid, comprising (a) a housing receptacle having a closed bottom end and an open top end, an interior surface of said receptacle defining (i) a lowermost upwardly diverging conical zone provided with liquid inlet means extending from a tip of said control zone through the bottom end of said receptacle, (ii) a first essentially cylindrical zone surmounting said conical zone and (iii) a second essentially cylindrical zone surmounting said first essentially cylindrical zone and having a cross-sectional diameter greater than that of said first essentially cylindrical zone and being in communicating relationship therewith, said conical zone and said first essentially cylindrical zone defining a chamber for the dissolution of a solid substance in a liquid solvent, a solid substance disposed in said chamber, (b) means flowing a liquid solvent into and through said cell, (c) a closure leakproofedly secured to the open end of said receptacle and provided with solute outlet means, and (d) filtration means arranged to engage said interior surface of said receptacle at a region of communicating relationship between said first and said second essentially cylindrical zones, so as to be disposed in a pathway for the solute extending from said dissolution chamber to said solute outlet means, said closure including means engaging said filtration means to maintain said filtration means in engagement with said interior surface of said receptacle.

2. The dissolution cell as defined by claim 1, said first and said second essentially cylindrical zones communicating via a shoulder element therebetween, said filtration means engaging said shoulder element.

3. The dissolution cell as defined by claim 2, said conical zone comprising a packing adapted to uniformly distribute said liquid solvent therethrough.

4. The dissolution cell as defined by claim 2, including leakproofing means secured between said shoulder and said filtration means, or between said filtration means and said closure.

5. The dissolution cell as defined by claim 1, said filtration means comprising a tubular filter.

6. The dissolution cell as defined by claim 5, said tubular filter comprising glass microfibers.

7. The dissolution cell as defined by claim 1, said closure being securedly affixed to an external periphery of the top end of said receptacle.

8. The dissolution cell as defined by claim 1, said closure comprising passageway means and at least one measurement probe extending therethrough into said dissolution chamber.

9. The dissolution cell as defined by claim 1, said closure being securedly affixed to the internal surfaces within the top end of said receptacle.

10. The dissolution cell as defined by claim 1, said closure comprising a body and a head disposed below a collection zone formed between the head and the body.

11. The dissolution cell as defined by claim 1, said dissolution chamber comprising means for retaining a sample of said solid substance.

12. Apparatus for determining the kinetics of dissolution of a solid substance in a particular liquid, comprising a dissolution cell as defined by claim 1 and pumping means for uniformly delivering a supply of liquid solvent to the liquid inlet means of the conical zone of said dissolution cell.

13. The apparatus as defined by claim 12, said pumping means comprising at least two opposed pistons actuated by a cam revolving about an axis perpendicular to the axis of said pistons.

14. The apparatus as defined by claim 13, comprising return means operably connected to each piston.

* * * * *